US006646241B1

(12) United States Patent
Varma et al.

(10) Patent No.: US 6,646,241 B1
(45) Date of Patent: Nov. 11, 2003

(54) MICROWAVE-ASSISTED STEAM STERILIZATION OF DENTAL AND SURGICAL INSTRUMENTS

(75) Inventors: Ravi Varma, Louisville, CO (US); Worth F. Vaughan, Madison, WI (US)

(73) Assignee: Ecofriend Technologies, Inc., Louisville, CO (US)

( * ) Notice: Subject to any disclaimer, the term of this patent is extended or adjusted under 35 U.S.C. 154(b) by 62 days.

(21) Appl. No.: 10/071,340

(22) Filed: Feb. 8, 2002

(51) Int. Cl.[7] ............................... H05B 6/80; A61L 2/12
(52) U.S. Cl. ..................... 219/679; 219/682; 219/686; 219/687; 219/746; 219/759; 422/21; 422/298; 422/307
(58) Field of Search ................. 219/679, 687, 219/688, 682, 686, 756, 762, 731, 759, 476, 697; 422/21, 298, 299, 307

(56) References Cited

U.S. PATENT DOCUMENTS

| | | | | |
|---|---|---|---|---|
| 4,400,357 A | * | 8/1983 | Hohmann | 422/297 |
| 4,861,956 A | | 8/1989 | Courneya | 219/10.55 |
| 4,865,814 A | | 9/1989 | Childress | 422/116 |
| 5,019,359 A | | 5/1991 | Kutner et al. | 422/294 |
| 5,039,495 A | | 8/1991 | Kutner et al. | 422/299 |
| 5,407,641 A | * | 4/1995 | Katschnig et al. | 219/679 |
| 5,417,941 A | | 5/1995 | McNulty | 422/307 |
| 5,599,499 A | | 2/1997 | Held et al. | 422/21 |
| 5,607,612 A | | 3/1997 | Held et al. | 219/759 |
| 6,277,610 B1 | * | 8/2001 | Grae | 422/38 |

FOREIGN PATENT DOCUMENTS

WO    WO 00/57929    10/2000    ............. A61L/2/12

OTHER PUBLICATIONS

Swaddiwudhipong, W., Linlawan, P., Prasantong, R., Kitphati, R., Wongwatcharapaiboon, P., "A report of an Outbreak of Postoperative Endophthalmitis," *Journal of Medical Association*, vol. 83, No. 8, Aug. 2000, pp. 902–907.

Savagem N.W., Walsh, L.J., "The use of autoclaves in the dental surgery," *Australian Dental Journal*, vol. 40, No. 3, 1995, pp. 197–200.

(List continued on next page.)

*Primary Examiner*—Philip H. Leung
(74) *Attorney, Agent, or Firm*—Samuel M. Freund

(57) ABSTRACT

A surgical and dental instrument sterilizer is described. Liquid water is rapidly vaporized by microwave heating and steam is generated to attain a steam pressure of approximately 47 psi and a temperature of approximately 135° C. in the region of the articles to be sterilized. Micron-size waterdroplets are intermittently sprayed onto the articles which are arranged on a tray, from both the top and from underneath thereof so as to thoroughly wet the surfaces. A 30–90 s duration of droplet spray is followed by pulsed microwave irradiation of the top and underneath surfaces for a similar period, as an example; this is followed by a plurality of spray/microwave cycles. Sterilizing conditions in the sterilizer chamber are maintained in the presence of the water spray/microwave flashing cycles since introducing small aliquots of water will not affect the desired sterilizing condition provided by superheated steam augmented by microwave radiation necessary to kill microbes including spores; however arcing from metal instruments when subjected to microwave radiation is substantially reduced.

39 Claims, 4 Drawing Sheets

OTHER PUBLICATIONS

Burke, F.J.T., Coulter, W.A., Cheung, S.W., Palenik, C.J., "Autoclave performance and practitioner knowledge of autoclaves use: A Survey of selected UK practicees," *Quintessence International*, vol. 29, No. 4, 1998, pp. 231–238.

Zaidi, M., Angulo, M., Sifuentes–Osornio, J., "Disinfection and sterilization practices in Mexico," *The Hospital Infection Society*, vol. 31, Apr. 25, 1995, pp. 25–32.

Yeo, C.B.A., Watson, I.A., Stewart–Tull, D.E.S., Koh, V.H.H., "Heat transfer analysis of Staphylococcus aureus on stainless steel microwave radiation," *Journal of Applied Microbiology*, vol. 87, 1999, pp. 396–401.

Abou–Kasm, E., Braats, B.G., Hill, D., Ishii, T.K., "Influence of moisture on Microwave arcing," International Symposium on Microwave Technology in Industrial Decelopment, Brazil, Jul. 22–25, 1985 ANAIS Proceedings, pp. 393–396.

\* cited by examiner

MICROWAVE-ASSISTED STEAM STERILIZATION OF DENTAL AND SURGICAL INSTRUMENTS

FIELD OF THE INVENTION

The present invention relates generally to sterilization of instruments and, more particularly, to the combined application of microwave and thermal energy in the presence of steam and liquid water to the sterilization of dental and surgical instruments and other objects.

BACKGROUND OF THE INVENTION

Several instrument sterilization procedures are presently in use. Autoclaving is most commonly employed, but slowly dulls sharp metal instruments. In U.S. Pat. No. 4,865,814 for "Automatic Sterilizer" which was issued to Bobby B. Childress on Sep. 12, 1989 a microprocessor-controlled heater which generates steam inside of a sealed chamber is described. The pressure level rather than the temperature is used to control the heater. Air is caused to be displaced from the sterilization chamber by the generation of the steam; however, this process does not remove all of the air. The presence of air interferes with production and maintenance of steam at the optimally desired temperature and pressure in the chamber and causes corrosion. Instances of failed sterilization using steam sterilizers are common. Such instances may be triggered by admixture of steam by trace air.

In "A Report Of An Outbreak Of Postoperative Endophthalmitis" by W. Swaddiwudhipong et al., J. Med. Assoc. Thailand 83, 902 (2000) defects in surgical sterilization including possible inadequacy in the autoclave sterilization of surgical instruments is reported. In "The Use Of Autoclaves In The Dental Surgery" by N. W. Savage and L. J. Walsh, Australian Dental Journal 40, 197 (1995), the authors state that although autoclaving is the absolute method of achieving instrument sterilization in any health-care setting, its effectiveness relies on an effective pre-sterilization routine for instrument handling and the subsequent correct loading and operating of the autoclaves. Similar findings are reported in "Autoclave Performance And Practitioner Knowledge Of Autoclave Use: A Survey Of Selected UK Practices" by F. J. T. Burke et al., Quintessence International 29, 231 (1998). In "Disinfection And Sterilization Practices In Mexico" by M. Zaidi et al., J. Hospital Infection 31, 25 (1995), the authors report the use of too short an exposure time in steam sterilizers or dry heat sterilizers as contributing to ineffective sterilization of surgical instruments.

Heat sterilization at approximately 160° C. is also used. However, this method requires heat generators capable of rapid heating which are not commonly available, and rubber and plastic parts may be damaged. Chemical sterilization techniques have the disadvantage that hazardous materials such as ethylene oxide or alkaline glutaraldehyde must be handled and disposed of in a hospital or dental clinic environment. Moreover, sterilization times are lengthy.

Sterilization of medical and dental instruments by directly and indirectly using microwaves is known. In both U.S. Pat. No. 5,019,359 for "Method And Apparatus For Rapid Sterilization Of Material" which was issued to Barry S. Kutner et al. on May 28, 1991 and U.S. Pat. No. 5,039,495 for "Apparatus For Sterilizing Articles Such As Dental Handpieces" which was issued to Barry S. Kutner et al. on Aug. 13, 1991, a liquid sterilant solution and the material to be sterilized are placed in a sealable, vapor-impermeable collapsible pouch. Microwave energy vaporizes the sterilant solution and the instruments are exposed either to the vaporized sterilant alone or to both microwave radiation and the vaporized sterilant. The vaporized sterilant prevents arcing and assists in sterilizing the instruments when used in conjunction with the microwaves. In U.S. Pat. No. 5,417,941 for "Microwave Powered Steam Pressure Generator" which issued to Bernard A. McNulty on May 23, 1995, an apparatus which produces high temperature and pressure steam derived from microwave energy is described. Microwave energy is coupled into a guiding structure such that essentially all of the energy is transferred to a reaction fluid contained in a holder located at the end of the guiding structure. The reaction fluid is rapidly vaporized and the resulting vapors expand into a high-pressure chamber through a metal screen that also prevents transmission of microwave energy. No mention is made of whether the resulting temperature and pressure permit steam sterilization to occur, whether the sterilization chamber is free of air during the sterilization cycle, or whether arcing of the metal parts is avoided.

In "Nonthermal Killing Effect Of Microwave Irradiation" by Seigo Sato et al., Biotech. Techniques 10, 145 (1996), the elucidation of the lethal effects of microwave radiation at constant temperatures is described. It was found that the death rates for *E. coli* exposed to microwave irradiation were higher than those obtained in conventional heat sterilization at the same temperatures. In "Heat Transfer Analysis Of *Staphylococcus aureus* On Stainless Steel With Microwave Radiation" by C. B. A. Yeo et al., J. Appl. Microbiol. 87, 396 (1999), the authors show that the microwave killing pattern of Staph. aureus is principally due to heat transfer from the stainless steel substrate which absorbs microwave energy in the surface regions, and that little direct energy is absorbed by the microbes from the incident microwave radiation. Complete bacterial inactivation was achieved at 61.4° C. with an irradiation time of 110 s.

Metallic instruments are problematic in microwave-assisted sterilization processes because such instruments reflect microwave energy and, when placed in microwave field, will arc. In U.S. Pat. No. 5,599,499 for "Method Of Microwave Sterilizing A Metallic Surgical Instrument While Preventing Arcing" which was issued to Jeffery S. Held and Robert F. Schiffmann on Feb. 4, 1997, and in U.S. Pat. No. 5,607,612 for "Container For Microwave Treatment Of Surgical Instrument With Arcing Prevention" which was issued to Jeffery S. Held and Robert F. Schiffmann on Mar. 4, 1997, a container for preventing arcing of a metal object placed therein and subjected to microwave radiation is described. To reduce arcing between metal surgical instruments, the container includes a tray upon which the instruments are located a suitable distance apart. Moreover, the container has at least one surface for absorbing microwave energy which impinges on the exterior surfaces of the container for converting the absorbed microwave radiation into heat that sterilizes the instruments. Iron oxide (that is, $Fe_2O_3$) materials are employed for this purpose, and prevent substantially all of the microwave radiation impinging on the exterior surface of the container from entering the volume of space therein.

In U.S. Pat. No. 4,861,956 for "Microwave/Steam Sterilizer" which issued to Calice G. Courneya on Aug. 29, 1989 a microwave/steam sterilizer is disclosed. The authors state that the sterilizer hydrates potential pathogens, including spores, and subjects them to relatively uniform electromagnetic energy without arcing and without self-destruction of the microwave source from reflected microwave energy.

According to Courneya et al. microwave energy is used to vaporize water forming steam which is rapidly absorbed by dry spores making them vulnerable to killing by direct microwave energy. The water vapor also keeps electrical charges sufficiently low that arcing and sparking are overcome. The sterilizer provides an adequate availability of water, as steam, to allow the dry spores to hydrate without flooding with excess water which acts as a coolant and prevents the formation of super-heated steam internally within the spores. Expected sterilizer temperatures are in the region of 98.9° C. Excess steam is preferentially attracted to the coolest area in the chamber, namely, the chamber walls. Thus, liquid water is not present on the instruments being sterilized. Additionally, 98.9° C. and steam at near atmospheric pressure are inadequate for sterilization of instruments based on experience with autoclaves.

In "A Microwave Based Device For Sterilisation/Disinfection Of Surgical And Dental Equipment" by Peter Nielsen et al., PCT/DK00/00146 having an International Publication Date of Oct. 5 2000, the inventors describe two embodiments of a microwave-based sterilizer. In one embodiment, tools are placed on trays and irradiated using microwave radiation. In the second embodiment, tools are placed in a sealed chamber which is placed in a volume into which microwaves are introduced. A steam condenser in fluid communication with the chamber is located outside of the volume and permits steam generated from a water reservoir within the chamber to be removed from the chamber, condensed and returned to the reservoir to enable the generation of additional steam. A desired pressure of 3 atm at 130° C. is taught.

In "Influence Of Moisture On Microwave Arcing" by Elias J. Abou-Kasam et al., International Symposium on Microwave Technology In Industrial Development, Brazil, Jul. 22–25 1985, ANAIS Proceedings, pages 393–396, 13100-Campinas, Sao Paulo, Brazil, the authors state that moist air reduces the electric field around metallic objects; the higher the humidity, the higher the threshold microwave power for arcing. The effect on the electric field of a liquid water layer on the metal objects is not discussed.

As will be discussed hereinbelow, if a film of water (dielectric constant, $\epsilon_{water}$, ≈46 at 135° C. and 47 psi at 2.45 GHz) is present on the metallic object, for the same incident microwave power the electric field experienced by the object will be significantly reduced when compared with the electric field expected for the same object disposed in an environment of superheated steam ($\epsilon_{steam}$ ≈1.01) at the same temperature, pressure and microwave frequency (see, e.g., F. Buckley and A. A. Maryott in NBS Circular 589 (1958)). From page 41 of Dielectrics and Waves by A. von Hippel, Wiley, N.Y. (1954), the microwave power equation is given by $P \propto \epsilon E^2$, where $\epsilon$ is the dielectric constant of the medium in which microwave power, P, is incident and E is the electric field therein. From this equation one may observe that for the same applied microwave power, $E^2_{steam}/E^2_{water} = \epsilon_{water}/\epsilon_{steam} \approx 46/1.01$, where $E_{steam}$ is electric field experienced by a metal object in the presence of steam and $E_{water}$ is the electric field experienced by that same object when coated with water, from which $E_{steam}/E_{water} \approx 7$. Thus, the electric field experienced by a water coated object is seven times smaller than that experienced by the same object in the presence of steam, and the likelihood of arcing is correspondingly reduced.

Accordingly it is an object of the present invention to provide an apparatus and method for effectively sterilizing surgical and dental instruments using a combination of microwave radiation and thermal energy in the presence of both steam and liquid water without arcing.

It is also an object of the present invention to provide an apparatus and method for effectively sterilizing surgical and dental instruments using a combination of microwave radiation and thermal energy in the presence of both steam and liquid water without arcing, where air is substantially removed from the vicinity of the instruments before the sterilization process.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the sterilization apparatus hereof includes: a sealed chamber capable of withstanding internal pressure and vacuum and having a sealable opening for introducing and removing items to be sterilized; a tray disposed within the chamber for holding items to be sterilized; at least one microwave radiation generator; microwave waveguide for directing microwave radiation generated by the at least one microwave radiation generator onto the items to be sterilized in said chamber; a pump for removing air from the chamber before microwave energy is directed onto the items to be sterilized; means for generating steam at greater than one atmosphere of pressure in the chamber; and a sprayer for directing droplets of water onto the items to be sterilized.

Preferably, means are provided for removing steam from the chamber after the sterilization process.

Preferably also, means are provided for cooling the items to be sterilized after the sterilization process.

In another aspect of the present invention in accordance with its objects and purposes the sterilization method hereof includes the steps of: placing the items to be sterilized in a sealed chamber capable of withstanding internal pressure and vacuum; evacuating the chamber to remove substantially all of the air therein; generating steam at greater than one atmosphere of pressure in the chamber; directing pulsed microwave radiation onto the items to be sterilized; and directing droplets of water onto the items to be sterilized.

Preferably, the steam is removed from the chamber after the sterilization process is completed and the items to be sterilized are cooled.

Preferably also, removing the steam from the chamber after the sterilization process is completed and cooling the items to be sterilized is accomplished by flowing dry nitrogen over the items to be sterilized.

Benefits and advantages of the present invention include rapid and complete sterilization of surgical and dental tools and other appliances without arcing.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings:

FIG. 4a is a cutaway schematic side view of the rapid opening and sealing mechanism for the lid of the pressure and vacuum compatible lid of the present invention, while

DETAILED DESCRIPTION

Briefly, the present invention includes a one or two cylindrical chamber surgical and dental instrument sterilizer. After evacuation of the sealed chamber to remove substantially all of the air therein, liquid water is rapidly vaporized by microwave heating with steam being generated at $\geq 47$ psi and a temperature of $\geq 135°$ C. in the vicinity of the instruments to be sterilized. Micron-size, water-droplets are intermittently sprayed onto the instruments, which are arranged on a tray, from both the top and from underneath so as to thoroughly wet the instrument surfaces. A 30–90 s duration of droplet spray is followed by pulsed microwave irradiation of the top and underneath surfaces of the instruments for a similar duration, as an example; the sterilization process includes a plurality of such spray/microwave cycles. Sterilizing conditions in the sterilizer are maintained in the presence of the water spray/microwave flashing cycles since introducing small aliquots of water will not affect the desired sterilizing condition provided by superheated steam augmented by microwave radiation necessary to kill microbes including spores; however, arcing from the surfaces of the surgical and dental instruments that are a exposed to microwave radiation during the sterilization cycle is significantly reduced or entirely eliminated by the presence of liquid water.

Figure 1:
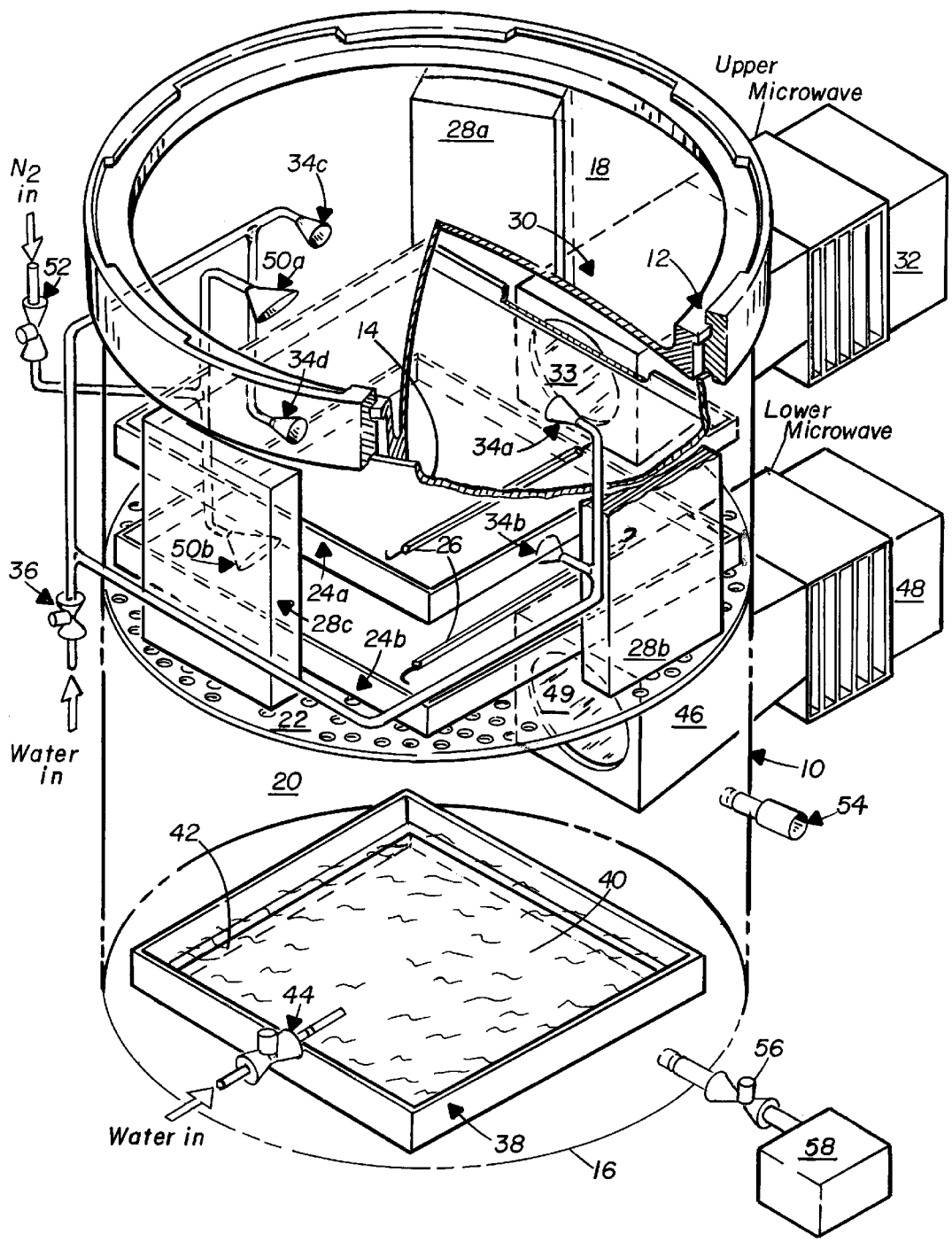
FIG. 1 is a schematic representation of the sterilizer of the present invention illustrating the use of two independent microwave sources, one for vaporizing the water and the other for providing microwave energy to the instruments to be sterilized.

Reference will now be made in detail to the present preferred embodiments of the inventions, examples of which are illustrated in the accompanying drawings. In the Figures, similar structure will be identified using identical callouts. Turning now to FIG. 1, the embodiment of the present invention employing two independent microwave sources is schematically illustrated. Generally cylindrical chamber, 10, adapted to be internally pressurized to $\geq 47$ psi and internally heated to $\geq 135°$ C., is shown to have a sealable, removable, pressure and vacuum compatible lid, 12, which sealably communicates with part of the upper portion of wall, 14, thereof, and a closed lower portion, 16. It should be mentioned that chamber 10 may be any shape and material that can withstand internal pressure >47 psi, heat $\geq 135°$ C., and internal vacuum, as will be discussed hereinbelow. Preferably, chamber 10 and lid 12 are fabricated from stainless steel, although other strong, temperature and steam resistant materials may be employed. Chamber 10 is divided into two volumes, 18 and 20, separated by metallic screen, 22, which is adapted to allow steam to freely pass between volumes 18 and 20, but not allow microwave energy to pass therebetween. Upper volume, 18, contains removable trays, 24a and 24b, upon which the items to be sterilized, 26, are placed, and through which steam and microwaves can pass; electrical heater means, 28a–c, for rapidly heating the vicinity of the instruments to a desired temperature; means, 30, for directing microwave energy generated by pulsed microwave radiation source, 32, onto the items to be sterilized 26 from above and below these items (Window, 33, isolates the microwave source from the harsh environment within chamber 10.); and spray apparatus, 34a–d, for spraying a pulsed, fine stream of water droplets onto the items to be sterilized controlled by water control valve, 36. Trays 24a and 24b are fabricated from microwave transparent materials such as fluorinated polyethylene tetraphthalate (PTFE). It is anticipated that an output power level between 800 W and 1200 W at 2.45 GHz should be sufficient for microwave radiation source 32. Other microwave frequencies can be used with similar results, but significant technology has developed around 2.45 GHz making equipment at this frequency readily available. Lower volume 20 contains water vessel, 38, for holding water, 40, which optionally rests on SiC plate, 42; means, 44, for maintaining the water, in vessel 38 at a constant level; means, 46, for directing microwave radiation generated by microwave source, 48, into the vicinity of vessel 38, such that steam is generated by the absorption of microwave radiation by water 40 and from conduction of heat from the absorption of microwave radiation by SiC plate 42. Window, 49, isolates the microwave source from the harsh environment within chamber 10. Fused silica is the preferred material for this window although any material which transmits microwave radiation and can withstand the pressure, temperature and vacuum of the chamber can be used. The purpose of metallic screen 22 is to prevent the high levels of continuous microwave radiation present in lower volume 20 which are required to vaporize water 40 from causing arcing by the items to be sterilized when the liquid water coating thereon is allowed to periodically evaporate in upper volume 18.

After the sterilization process is complete, dry nitrogen gas is caused to flow over the items to be sterilized 26 through jets, 50a and 50b, by gas control valve, 52, and is vented to the outside through escape valve, 54. This serves the dual function of rapidly cooling the items to be sterilized and driving the steam out of vessel 10. Vessel 10 can also be evacuated through valve, 56, using vacuum pump, 58. This permits the removal of substantially all of the air in vessel 10 before the sterilization process is begun and allows the sterilization conditions of a steam pressure of $\geq 47$ psi at a temperature $\geq 135°$ C. to be achieved.

Figure 2:
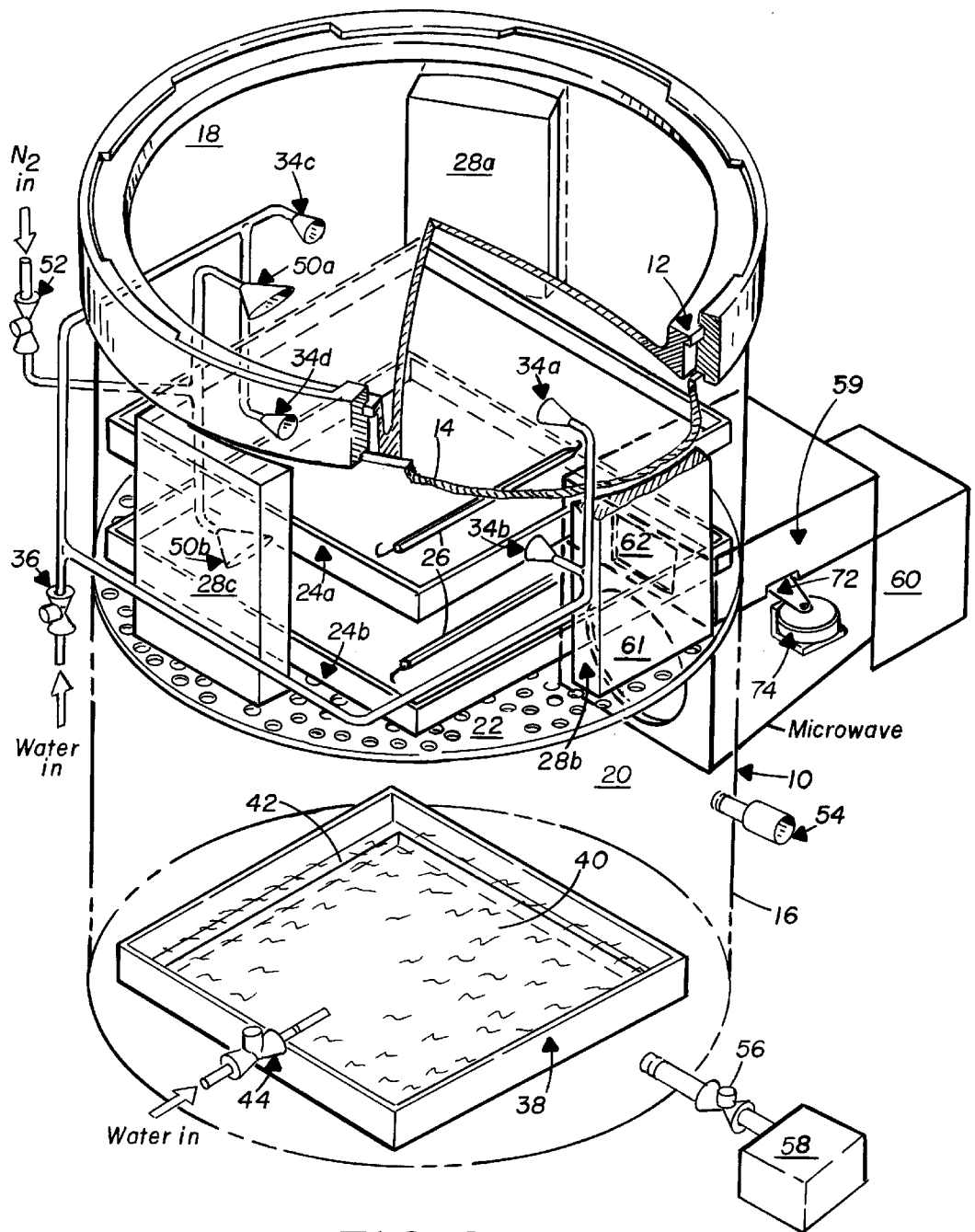
FIG. 2 is a schematic representation of the sterilizer of the present invention illustrating the use of a single microwave source employed in cooperation with a microwave beam splitter for both vaporizing the water and for providing microwave energy to the instruments to be sterilized.

FIG. 2 shows an embodiment of the present invention illustrating similar components to those shown in FIG. 1 hereof, but utilizing a single microwave source, 60, for both heating the water 40 in vessel 38, and for irradiating the items to be sterilized 26 in trays 24a and 24b . Microwave beamsplitter, 59, receives microwave radiation from source 60 and divides the radiation into two portions: one for heating water 40 in vessel 38 which is directed through window, 61, and the other for the pulsed irradiation of the items to be sterilized 26 which is directed through window, 62. Windows 61 and 62 protect beamsplitter 59 and microwave source 60 from the harsh environment of vessel 10.

Figure 3:
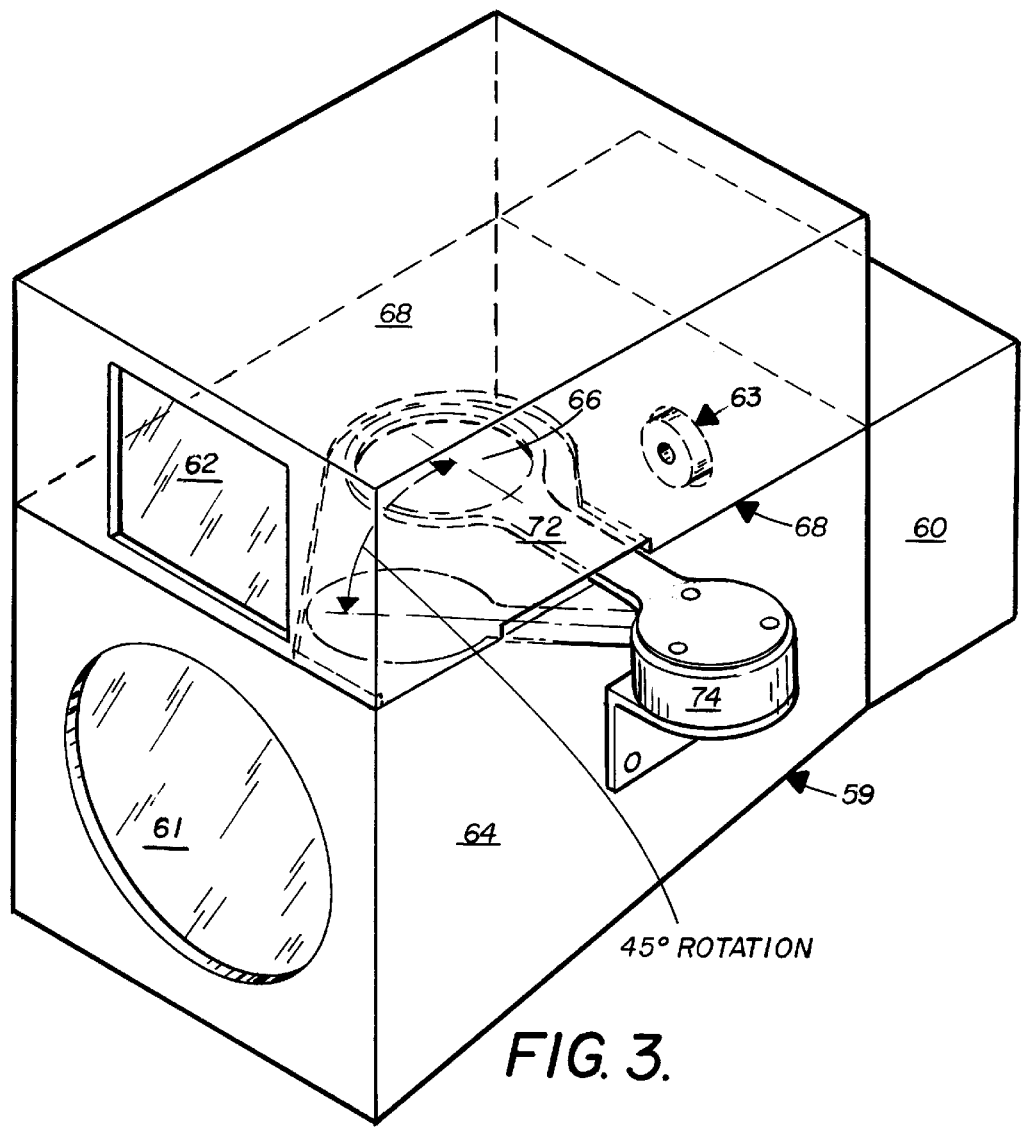
FIG. 3 is a cutaway schematic representation of the microwave beam splitter described in FIG. 2 hereof.

The pulsed irradiation of the items to be sterilized is achieved using a motor driven vane described in FIG. 3 hereof. FIG. 3 shows a schematic representation of microwave beamsplitter 59. As stated hereinabove, beamsplitter 59 divides the microwave radiation passing through source window, 63, from microwave source 60 into two portions. This is accomplished by employing a beamsplitter having two microwave waveguide chambers sharing a common wall. A first chamber, 64, directs continuous microwave radiation through window 61 for generating steam in vessel 10. Hole, 66, in the wall of chamber 64 permits microwave energy to enter second chamber, 68 which channels the entering radiation through window 62 and onto the items to be sterilized. Windows 61 and 62 can be fabricated from any material that transmits microwave radiation and can withstand the pressure, temperature and vacuum experienced by the sterilization chamber. Fused silica is one preferred material for this purpose. Metal vane, 72, actuated by motor, 74, to open and close hole 66 provides the desired pulsed microwave irradiation of items 26. It is anticipated that an output power of between 800 W and 1200 W at 2.45 GHz from microwave source 60 will be sufficient to accomplish both functions when approximately 75% of the power is utilized for heating the water and 25% is directed onto the instruments to be sterilized.

Figure 4A:
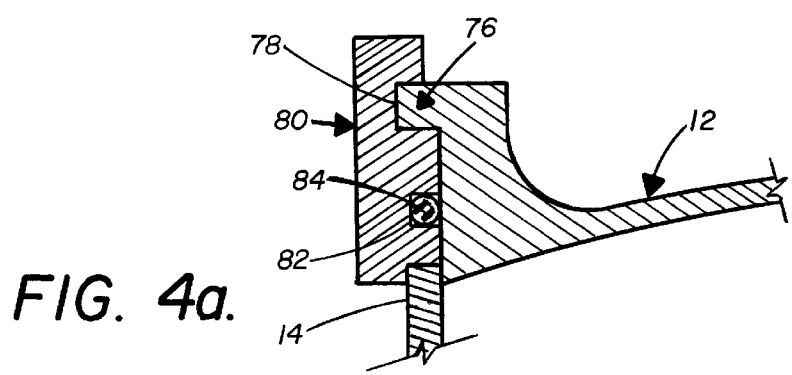
Figure 4B:
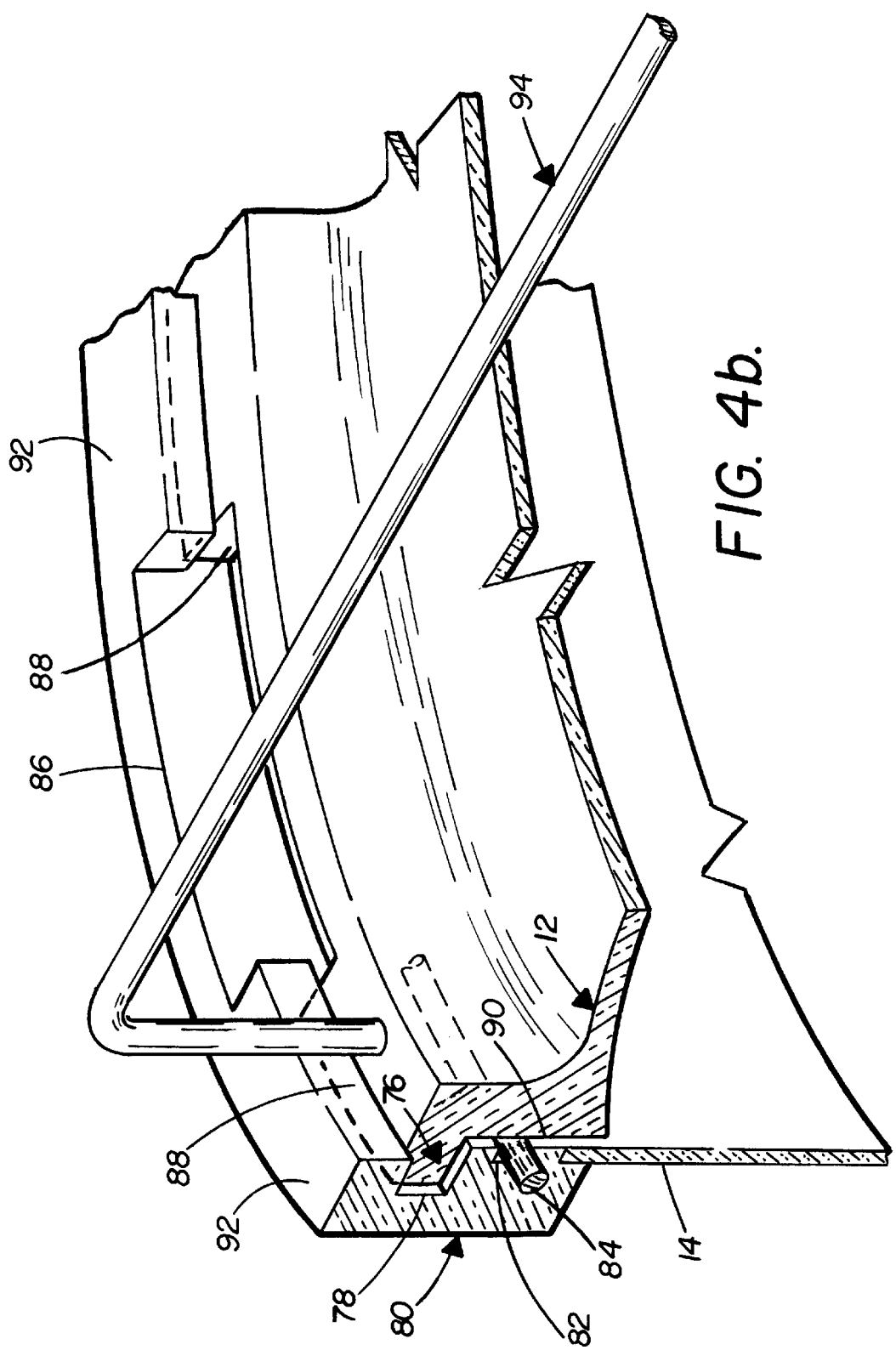
FIG. 4b is a cutaway schematic projection view thereof.

Turning now to FIGS. 4a and 4b hereof, cutaway views of removable, sealable pressure and vacuum compatible lid 12 of FIGS. 1 and 2 hereof are schematically illustrated. As stated hereinabove, circular lid 12 of chamber 10 includes segmented lip, 76, adapted to be received by groove, 78, in flange, 80, which is sealably secured to wall 14 and which also includes o-ring groove, 82, adapted to receive sealing o-ring, 84. The part of flange 80 located above groove 78 is cut away in a sufficient number of locations, 86, such that when the segments, 88, of segmented lip 76 of lid 12 are correctly oriented and the pressure inside of chamber 10 is approximately equal to that outside of the chamber, lid 12 can be lifted off of chamber 10 in order to gain access thereto. Lid 12 can be locked into place by first aligning segments 88 with cutaway portions 86 of flange 80 and positioning the lid such that wall 90 of lid 12 contacts o-ring 84, then rotating the lid either clockwise or counterclockwise about its axis until segments 88 are captured by solid portions, 92, in groove 78 of flange 80. Handle, 94, facilitates the required movements of flange 12. Lid 12 is shown to be dish-shaped in order that it better withstand the forces of pressure and vacuum within chamber 10.

A typical operating cycle of the sterilization chamber of the present invention is as follows:

(a) The articles to be sterilized are first loaded onto the trays which are then placed in the sterilization chamber, the chamber is sealed by closing the lid and the interior of the chamber which contains air at ambient pressure is evacuated;

(b) After evacuation, the water is introduced into the water tray in the chamber and the magnetron or magnetrons and auxiliary heaters are activated;

(c) The system temperature and pressure are monitored until the saturated steam reaches a temperature and pressure close to 135° C. and 47 psi, respectively, which is expected to take approximately 15 min.;

(d) The articles to be sterilized are sprayed with liquid water at a chosen duty cycle, for example, between 30 s and 90 s, and then irradiated using pulsed microwave radiation for a similar period during the time when the spray process is not taking place, the subsequent spray and irradiation steps forming one cycle;

(e) After a chosen number of spray/irradiation cycles, the steam is either pumped out or displaced by nitrogren gas and nitrogen gas or dry air is flowed over the instruments at ambient pressure until the instruments reach a temperature of about 40° C.

It is expected that the sterilization process should take approximately 20 min.

The foregoing description of the invention has been presented for purposes of illustration and description and is not intended to be exhaustive or to limit the invention to the precise form disclosed, and obviously many modifications and variations are possible in light of the above teaching. For example, the chamber may have other than cylindrical shape so long as it can withstand temperatures in excess of 135° C. and pressures in excess of 47 psi. Moreover the SiC tray can be replaced by any microwave-absorbing high-temperature material; for example, ferrous-ferric oxide, $Fe_3O_4$. In addition to metallic items, the articles to be sterilized may also include ceramic or plastic materials that can tolerate the sterilization conditions set forth hereinabove.

The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A sterilization apparatus comprising in combination:
   (a) a sealed first chamber capable of withstanding internal pressure and vacuum and having a sealable opening for introducing and removing articles to be sterilized;
   (b) at least one tray disposed within said first chamber for holding items to be sterilized;
   (c) a first microwave radiation generator;
   (d) a first waveguide for directing microwave radiation generated by said first microwave radiation generator onto the articles to be sterilized;
   (e) a sprayer for directing droplets of water onto the articles to be sterilized;
   (f) means for generating steam at greater than one atmosphere of pressure and for introducing the steam into said first chamber; and
   (g) a pump for evacuating said first chamber before the steam is introduced thereto and for removing the steam after the sterilization process is completed.

2. The apparatus as described in claim 1, further comprising means for cooling the articles to be sterilized after the sterilization process is completed.

3. The apparatus as described in claim 2, wherein said means for rapidly cooling the items to be sterilized comprises means for directing a stream of nitrogen over the articles to be sterilized.

4. The apparatus as described in claim 2, wherein said means for rapidly cooling the items to be sterilized comprises means for directing a stream of air over the articles to be sterilized.

5. The apparatus as described in claim 1, further comprising heaters located within said first chamber for rapidly bringing the temperature of the interior of said first chamber to a desired value and for maintaining the interior of said first chamber at the desired value.

6. The apparatus as described in claim 5, wherein said heaters are resistive heaters.

7. The apparatus as described in claim 1, wherein said at least one tray is fabricated from microwave transparent material.

8. The apparatus as described in claim 7, wherein the microwave transparent material comprises fluorinated polyethylene tetraphthalate.

9. The apparatus as described in claim 1, wherein said first waveguide is isolated from said first chamber by a first microwave window capable of transmitting microwave radiation and withstanding the pressure, temperature and vacuum within said first chamber.

10. The apparatus as described in claim 9, wherein said first microwave window comprises fused silica.

11. The apparatus as described in claim 1, wherein said means for generating steam at greater than one atmosphere of pressure and for introducing the steam into said first chamber comprises a second sealed chamber in contact with and located vertically below said first chamber, the contact between said first chamber and said second chamber being achieved by a horizontally disposed, perforated metal wall capable of passing steam but not microwave radiation, said first chamber and said second chamber together being capable of withstanding internal pressure and vacuum; an open vessel for containing water; and means for heating the water in said open vessel, thereby generating steam.

12. The apparatus as described in claim 11, wherein said means for heating the water comprises a second microwave radiation generator and a second microwave waveguide for directing microwave radiation generated by said second microwave generator into said second chamber such that the water is heated.

13. The apparatus as described in claim 12, wherein said second waveguide is isolated from said second chamber by a second microwave window capable of transmitting microwave radiation and withstanding the pressure, temperature and vacuum within said second chamber.

14. The apparatus as described in claim 13, wherein said second microwave window comprises fused silica.

15. The apparatus as described in claim 12, further comprising a layer of SiC in thermal contact with said vessel for containing water for enhancing the absorption of microwave energy from said second microwave radiation generator.

16. The apparatus as described in claim 12, further comprising a layer of $Fe_3O_4$ in thermal contact with said vessel for containing water for enhancing the absorption of microwave energy from said second microwave radiation generator.

17. The apparatus as described in claim 11, wherein said means for heating the water comprises a microwave beamsplitter for receiving microwave radiation generated by said first microwave generator and directing a first portion of the microwave radiation into said first chamber and onto the articles to be sterilized such that the articles are sterilized, and directing a second portion of the microwave radiation into said second chamber and onto the open vessel for containing water, such that the water is heated, thereby generating steam.

18. The apparatus as described in claim 17, wherein said microwave beamsplitter comprises:
(a) a third rectangular waveguide having walls, for receiving a first portion of microwave radiation and for directing the first portion of the microwave radiation into said first chamber and onto the articles to be sterilized;
(b) a fourth rectangular waveguide having walls, for receiving microwave radiation generated by said first microwave generator and directing a second portion of the microwave radiation into said second chamber and onto the open vessel for containing water, said third waveguide and said fourth waveguide sharing a common wall;
(c) a mechanical shutter for periodically opening and closing an opening in the wall shared by said third waveguide and said fourth waveguide, thereby switching the first portion of microwave radiation received by said third waveguide on and off such that the microwave radiation reaching the articles to be sterilized is pulsed; and
(d) an electrical motor for driving said mechanical shutter.

19. The apparatus as described in claim 18, wherein said microwave beamsplitter further comprises:
(a) a third microwave window adapted to transmit the first portion of microwave radiation and disposed between said first chamber and said third waveguide; and
(b) a fourth microwave window adapted to transmit the second portion of microwave radiation and disposed between said second chamber and said fourth waveguide, said third microwave window and said fourth microwave window being capable of isolating said third waveguide and said fourth waveguide from the pressure, temperature and vacuum within said first chamber and said second chamber, respectively.

20. The apparatus as described in claim 19, wherein said first window and said second window comprise fused silica.

21. The apparatus as described in claim 17, further comprising a layer of SiC in thermal contact with said vessel for containing water for enhancing the absorption of microwave energy from said second microwave radiation generator.

22. The apparatus as described in claim 17, further comprising a layer of $Fe_3O_4$ in thermal contact with said vessel for containing water for enhancing the absorption of microwave energy from said second microwave radiation generator.

23. The apparatus as described in claim 17, wherein steam is generated at a pressure of >47 psi and a temperature of $\geq 135°$ C.

24. The apparatus as described in claim 17, wherein the articles to be sterilized are constructed from materials selected from the group consisting of metallic, ceramic and plastic materials.

25. The apparatus as described in claim 1, wherein said first microwave radiation generator is a pulsed microwave radiation generator.

26. The apparatus as described in claim 1, wherein steam is generated at a pressure of $\geq 47$ psi and a temperature of $\geq 135°$ C.

27. The apparatus as described in claim 1, wherein the articles to be sterilized are constructed from materials selected from the group consisting of metallic, ceramic and plastic materials.

28. The apparatus as described in claim 1, wherein said first chamber further comprises:
(a) an outer cylindrical wall having an upper portion containing a first groove and a second groove located below the first groove in the inside surface of said outer cylindrical wall, the upper portion of said wall being cut away in a chosen number of places above the first groove, and the second groove being adapted to receive a sealing o-ring; and
(b) an o-ring, said sealable opening comprising:
(a) a circular lid having a segmented lip adapted to be received and captured by the first groove when the segments of said segmented lip of said lid are correctly oriented with the chosen number of cut away portions of the upper portion of said cylindrical chamber wall, and having a cylindrical wall adapted to sealably contact said o-ring; and
(b) means for rotating said circular lid.

29. The apparatus as described in claim 28, wherein said first chamber, said second chamber and said circular lid are fabricated out of stainless steel.

30. The apparatus as described in claim 28, wherein said circular lid is dish-shaped.

31. A method for sterilizing articles which comprises in order the steps of:
(a) placing the articles to be sterilized in a sealed chamber capable of withstanding internal pressure and vacuum;
(b) evacuating the chamber;
(c) introducing steam at greater than one atmosphere of pressure into the chamber;
(d) directing droplets of water onto the articles to be sterilized for a first chosen time period; and
(e) directing pulsed microwave radiation onto the articles to be sterilized for a second chosen time period after said first time period is completed, thereby producing sterilized articles.

32. The method as described in claim 31, further comprising the step of evacuating the steam from the chamber after the sterilization process is completed.

33. The method as described in claim 31, further comprising the step of cooling the sterilized articles.

34. The method as described in claim 33, wherein said step of cooling the articles to be sterilized comprises directing a stream of nitrogen over the articles to be sterilized.

35. The method as described in claim 33, wherein said step of cooling the articles to be sterilized comprises directing a stream of air over the articles to be sterilized.

36. The method as described in claim 31, further comprising the step of maintaining the interior of the chamber at a desired temperature.

37. The method as described in claim 31, wherein the steam is maintained at a pressure of $\geqq 47$ psi and a temperature of $\geqq 135°$ C.

38. The method as described in claim 31, wherein the articles to be sterilized are constructed from materials selected from the group consisting of metallic, ceramic and plastic materials.

39. The method as described in claim 31, wherein the first chosen time period is between 30 s and 90 s and the second chosen time period is between 30 s and 90 s.

* * * * *